United States Patent [19]
Gough et al.

[11] Patent Number: 5,728,143
[45] Date of Patent: *Mar. 17, 1998

[54] MULTIPLE ANTENNA ABLATION APPARATUS AND METHOD

[75] Inventors: Edward J. Gough, Menlo Park; Alan A. Stein, Moss Beach, both of Calif.

[73] Assignee: Rita Medical Systems, Inc., Mountain View, Calif.

[ * ] Notice: The term of this patent shall not extend beyond the expiration date of Pat. No. 5,672,174.

[21] Appl. No.: 605,323

[22] Filed: Feb. 14, 1996

Related U.S. Application Data

[63] Continuation-in-part of Ser. No. 515,379, Aug. 15, 1995.

[51] Int. Cl.$^6$ ................................................ A61B 17/39
[52] U.S. Cl. .................. 607/101; 607/102; 607/156; 606/41; 606/42
[58] Field of Search ............... 606/41, 42, 45–50; 607/115, 116, 100–102, 154, 156; 128/642; 604/22

[56] References Cited

U.S. PATENT DOCUMENTS

| | | |
|---|---|---|
| Re. 32,057 | 12/1985 | Leveen . |
| Re. 32,066 | 1/1986 | Leveen . |
| 3,991,770 | 11/1976 | Leveen . |
| 4,016,886 | 4/1977 | Doss . |
| 4,074,718 | 2/1978 | Morrison, Jr. . |
| 4,080,959 | 3/1978 | Leveen . |
| 4,095,602 | 6/1978 | Leveen . |
| 4,119,102 | 10/1978 | Leveen . |
| 4,140,130 | 2/1979 | Storm, III . |
| 4,154,246 | 5/1979 | Leveen . |
| 4,230,129 | 10/1980 | Leveen . |
| 4,285,346 | 8/1981 | Armitage . |
| 4,290,435 | 9/1981 | Waggott . |
| 4,303,636 | 12/1981 | Gordon . |
| 4,346,715 | 8/1982 | Cammell . |
| 4,375,220 | 3/1983 | Matvias . |
| 4,545,368 | 10/1985 | Rand et al. . |
| 4,565,200 | 1/1986 | Cosman . |
| 4,676,258 | 6/1987 | Inokuchi et al. . |
| 4,709,701 | 12/1987 | Weber . |
| 4,823,791 | 4/1989 | D'Amelio . |
| 4,881,543 | 11/1989 | Trembly et al. . |
| 4,887,614 | 12/1989 | Shirakami et al. . |
| 4,962,761 | 10/1990 | Golden . |
| 5,003,991 | 4/1991 | Takayama et al. . |
| 5,007,908 | 4/1991 | Rydell . |
| 5,010,897 | 4/1991 | Leveen . |
| 5,099,756 | 3/1992 | Franconi . |
| 5,190,517 | 3/1993 | Zieve et al. . |
| 5,190,541 | 3/1993 | Abele . |
| 5,257,451 | 11/1993 | Edwards . |

(List continued on next page.)

FOREIGN PATENT DOCUMENTS

WO 96/29946 10/1996 WIPO .

*Primary Examiner*—Lee S. Cohen
*Assistant Examiner*—Michael Peffley
*Attorney, Agent, or Firm*—Wilson Sonsini Goodrich & Rosati

[57] ABSTRACT

A multiple antenna ablation apparatus includes an electromagnetic energy source, a trocar including a distal end, and a hollow lumen extending along a longitudinal axis of the trocar, and a multiple antenna ablation device with three or more antennas. The antennas are initially positioned in the trocar lumen as the trocar is introduced through tissue. At a selected tissue site the antennas are deployable from the trocar lumen in a lateral direction relative to the longitudinal axis. Each of the deployed antennas has an electromagnetic energy delivery surface of sufficient size to, (i) create a volumetric ablation between the deployed antennas, and (ii) the volumetric ablation is achieved without impeding out any of the deployed antennas when 10 to 50 watts of electromagnetic energy is delivered from the electromagnetic energy source to the multiple antenna ablation device. At least one cable couples the multiple antenna ablation device to the electromagnetic energy source.

38 Claims, 8 Drawing Sheets

U.S. PATENT DOCUMENTS

| | | |
|---|---|---|
| 5,273,535 | 12/1993 | Edwards . |
| 5,275,162 | 1/1994 | Edwards . |
| 5,282,797 | 2/1994 | Chess . |
| 5,293,869 | 3/1994 | Edwards . |
| 5,309,910 | 5/1994 | Edwards . |
| 5,313,943 | 5/1994 | Houser . |
| 5,314,466 | 5/1994 | Stern . |
| 5,328,467 | 7/1994 | Edwards . |
| 5,334,193 | 8/1994 | Nardella . |
| 5,342,357 | 8/1994 | Nardella . |
| 5,348,554 | 9/1994 | Imran . |
| 5,363,861 | 11/1994 | Edwards . |
| 5,366,490 | 11/1994 | Edwards . |
| 5,368,592 | 11/1994 | Stern . |
| 5,370,675 | 12/1994 | Edwards . |
| 5,370,678 | 12/1994 | Edwards . |
| 5,383,917 | 1/1995 | Desai et al. ............................. 607/102 |
| 5,385,544 | 1/1995 | Edwards . |
| 5,398,683 | 3/1995 | Edwards . |
| 5,403,311 | 4/1995 | Abele et al. ............................. 606/49 |
| 5,409,453 | 4/1995 | Lundquist . |
| 5,421,819 | 6/1995 | Edwards . |
| 5,423,807 | 6/1995 | Milder . |
| 5,423,808 | 6/1995 | Edwards . |
| 5,423,811 | 6/1995 | Imran . |
| 5,433,708 | 7/1995 | Nichols . |
| 5,435,805 | 7/1995 | Edwards . |
| 5,437,662 | 8/1995 | Nardella . |
| 5,456,662 | 10/1995 | Edwards . |
| 5,456,682 | 10/1995 | Edwards . |
| 5,458,596 | 10/1995 | Lax . |
| 5,458,597 | 10/1995 | Edwards . |
| 5,462,521 | 10/1995 | Bruckner et al. . |
| 5,470,308 | 11/1995 | Edwards . |
| 5,470,309 | 11/1995 | Edwards . |
| 5,471,982 | 12/1995 | Edwards . |
| 5,472,441 | 12/1995 | Edwards . |
| 5,484,400 | 1/1996 | Edwards . |
| 5,486,161 | 1/1996 | Lax . |
| 5,505,730 | 4/1996 | Edwards . |
| 5,507,743 | 4/1996 | Edwards . |
| 5,509,419 | 4/1996 | Edwards . |
| 5,514,130 | 5/1996 | Baker . |
| 5,514,131 | 5/1996 | Edwards . |
| 5,531,676 | 7/1996 | Edwards . |
| 5,531,677 | 7/1996 | Lundquist . |
| 5,536,240 | 7/1996 | Edwards . |
| 5,536,267 | 7/1996 | Edwards . |
| 5,540,655 | 7/1996 | Edwards . |
| 5,542,915 | 8/1996 | Edwards . |
| 5,542,916 | 8/1996 | Hirsch . |
| 5,542,928 | 8/1996 | Evans . |
| 5,545,161 | 8/1996 | Imran . |
| 5,545,171 | 8/1996 | Sharkey . |
| 5,545,193 | 8/1996 | Fleischman . |
| 5,546,267 | 8/1996 | Frederiksen . |
| 5,549,108 | 8/1996 | Edwards . |
| 5,549,644 | 8/1996 | Lundquist . |
| 5,554,110 | 9/1996 | Edwards . |
| 5,556,377 | 9/1996 | Rosen . |
| 5,558,672 | 9/1996 | Edwards . |
| 5,558,673 | 9/1996 | Edwards . |
| 5,560,358 | 10/1996 | Arnold . |
| 5,562,703 | 10/1996 | Desai . |

MULTIPLE ANTENNA ABLATION APPARATUS AND METHOD

REFERENCE TO RELATED APPLICATION

This application is a continuation-in-part of U.S. patent application Ser. No. 08/515,379, filed Aug. 15, 1995, entitled "Multiple Antenna Ablation Apparatus", incorporated herein by reference.

BACKGROUND OF THE INVENTION

1. Field of the Invention

This invention relates generally to a multiple antenna ablation apparatus, and more particularly to a multiple antenna ablation apparatus where the size of the antennas' electromagnetic energy delivery surfaces is sufficient to prevent the apparatus from impeding out.

2. Description of the Related Art

Current open procedures for treatment of tumors are extremely disruptive and cause a great deal of damage to healthy tissue. During the surgical procedure, the physician must exercise care in not cutting the tumor in a manner that creates seeding of the tumor, resulting in metastasis. In recent years, development of products has been directed with an emphasis on minimizing the traumatic nature of traditional surgical procedures.

There has been a relatively significant amount of activity in the area of hyperthermia as a tool for treatment of tumors. It is known that elevating the temperature of tumors is helpful in the treatment and management of cancerous tissues. The mechanisms of selective treatment are not completely understood. However, four cellular effects of hyperthermia on cancerous tissue have been proposed, (i) changes in cell or nuclear membrane permeability or fluidity, (ii) cytoplasmic lysomal disintegration, causing release of digestive enzymes, (iii) protein thermal damage affecting cell respiration and the synthesis of DNA or RNA and (iv) potential excitation of immunologic systems. Treatment methods for applying heat to tumors include the use of direct contact radio-frequency (RF) applicators, microwave radiation, inductively coupled RF fields, ultrasound, and a variety of simple thermal conduction techniques.

Among the problems associated with all of these procedures is the requirement that highly localized heat be produced at depths of several centimeters beneath the surface of the skin. RF applications may be used at depth during surgery. However, the extent of localization is generally poor, with the result that healthy tissue may be harmed.

With RF lesion making, a high frequency alternating current flows from the electrode into the tissue. Ionic agitation is produced in the region of tissue about the electrode tip as the ions attempt to follow the directional variations of the alternating current. This agitation results in frictional heating so that the tissue about the electrode, rather than the electrode itself, is the primary source of heat. Tissue heat generated is produced by the flow of current through the electrical resistance offered by the tissue. The greater this resistance, the greater the heat generated.

Lesion size ultimately is governed by tissue temperature. Some idea of tissue temperature can be obtained by monitoring the temperature at an electrode or probe tip, usually with a thermistor. RF lesion heat is generated within the tissue, the temperature monitored will be the resultant heating of the electrode by the lesion. RF lesion heat is generated within the tissue, the temperature monitored is the resultant heating of the probe by the lesion. A temperature gradient extends from the lesion to the probe tip, so that the probe tip is slightly cooler than the tissue immediately surrounding it, but substantially hotter than the periphery of the lesion because of the rapid attenuation of heating effect with distance.

Current spreads out radially from the electrode tip, so that current density is greatest next to the tip, and decreases progressively at distances from it. The frictional heat produced from ionic agitation is proportional to current, i.e., ionic density. Therefore, the heating effect is greatest next to the electrode and decreases with distance from it. One consequence of this is that lesions can inadvertently be made smaller than anticipated for a given electrode size if the RF current level is too high. Them must be time for equilibrium heating of tissue to be reached, especially at the center of the desired lesion volume. If the current density is too high, the tissue temperature next to the electrode rapidly exceeds desired levels and carbonization and boiling occurs in a thin tissue shell surrounding the electrode tip.

A need exists for a multiple antenna ablation apparatus with antenna electromagnetic energy delivery surface areas that are sufficiently large enough to prevent the apparatus from impeding out. There is a further need for a multiple antenna ablation apparatus with a sufficient number of antennas, providing a large enough electromagnetic energy delivery surface to a selected tissue site, to achieve volumetric ablation without impeding out the apparatus.

SUMMARY OF THE INVENTION

Accordingly, it is an object of the invention to provide an ablation device which includes multiple antennas that are deployed from a trocar into a selected tissue site.

Another object of the invention is to provide a multiple antenna ablation apparatus with electromagnetic energy delivery surfaces that are large enough to prevent the apparatus from impeding out.

Yet another object of the invention is to provide a multiple antenna ablation apparatus with a sufficient number of antennas to provide a large enough electromagnetic energy delivery from the antennas to prevent the apparatus from impeding out.

Still a further object of the invention is to provide a multiple antenna RF ablation apparatus with antenna electromagnetic energy delivery surfaces sufficiently large to prevent the apparatus from impeding out.

These and other objectives are achieved in a multiple antenna ablation apparatus. The apparatus includes an electromagnetic energy source, a trocar including a distal end, and a hollow lumen extending along a longitudinal axis of the trocar, and a multiple antenna ablation device with three or more antennas. The antennas are initially positioned in the trocar lumen as the trocar is introduced through tissue. At a selected tissue site the antennas are deployable from the trocar lumen in a lateral direction relative to the longitudinal axis. Each of the deployed antennas has an electromagnetic energy delivery surface of sufficient size to, (i) create a volumetric ablation between the deployed antennas, and (ii) the volumetric ablation is achieved without impeding out any of the deployed antennas when 10 to 50 watts of electromagnetic energy is delivered from the electromagnetic energy source to the multiple antenna ablation device. At least one cable couples the multiple antenna ablation device to the electromagnetic energy source.

In another embodiment, a method for creating a volumetric ablation in a selected tissue mass provides a multiple antenna ablation apparatus including a trocar with a trocar lumen, a plurality of antennas deployable from the lumen, and an electromagnetic energy source coupled to the plurality of antennas. The trocar is inserted into the selected tissue mass with the plurality of antennas positioned in the trocar lumen. The plurality of antennas are advanced from the trocar lumen in a lateral direction relative to a longitudinal axis of the trocar into the selected tissue mass. 10 to 50 watts of electromagnetic energy is delivered from the electromagnetic energy source to the plurality of antennas without impeding out an antenna of the plurality of antennas. The volumetric ablation is created between the plurality of antennas.

In various embodiments, the apparatus can each of the antennas coupled to the electromagnetic energy source, only one antenna coupled to the electromagnetic energy source, or more than one antenna coupled. The trocar has an outer diameter of no greater than 13 gauge, preferably no greater than 14 gauge, and still more preferably no more than 15 gauge.

The number of deployed antennas can be four, five, six or more. Some of the antennas can be deployed out of the distal end of the trocar, while other antennas may be deployed from ports formed in the trocar along its longitudinal axis. The antennas may be RF electrodes operating in a monopolar mode, bipolar mode, or switchable between the two.

At least one sensor, preferably a thermal sensor, can be positioned along an exterior surface of a deployed antenna. More than one antenna can include a sensor. An insulation layer may be positioned in a surrounding relationship around at least a portion of an exterior of the trocar. A distal end of the insulation at the distal end of the trocar can be removed. This creates an electromagnetic energy delivery surface at the trocar's distal end. The trocar then becomes at least partially an antenna.

The trocar lumen may be coupled to an infusion medium source and deliver an infusion medium to the selected tissue site. A cooling element can be coupled to at least one of the antennas. The cooling element can be a structure positioned in at least one of the antennas and include at least one channel configured to receive a cooling medium. The cooling medium can be recirculated through the channel.

DETAILED DESCRIPTION

The present invention provides a multiple antenna ablation apparatus. The apparatus includes an electromagnetic energy source, a trocar including a distal end, and a hollow lumen extending along a longitudinal axis of the trocar, and a multiple antenna ablation device with three or more antennas. The antennas are initially positioned in the trocar lumen as the trocar is introduced through tissue. At a selected tissue site the antennas are deployable from the trocar lumen in a lateral direction relative to the longitudinal axis. Each of the deployed antennas has an electromagnetic energy delivery surface of sufficient size to, (i) create a volumetric ablation between the deployed antennas, and (ii) create the volumetric ablation without impeding out any of the deployed antennas when 10 to 50 watts of electromagnetic energy is delivered from the electromagnetic energy source to the multiple antenna ablation device. At least one cable couples the multiple antenna ablation device to the electromagnetic energy source. For purposes of this specification the term "impeding out" means that a tissue area has become sufficiently desiccated or carbonized that the desiccated or carbonized tissue area has a resultant high electrical resistance that impairs the process of creating a coagulating lesion.

Figure 1:
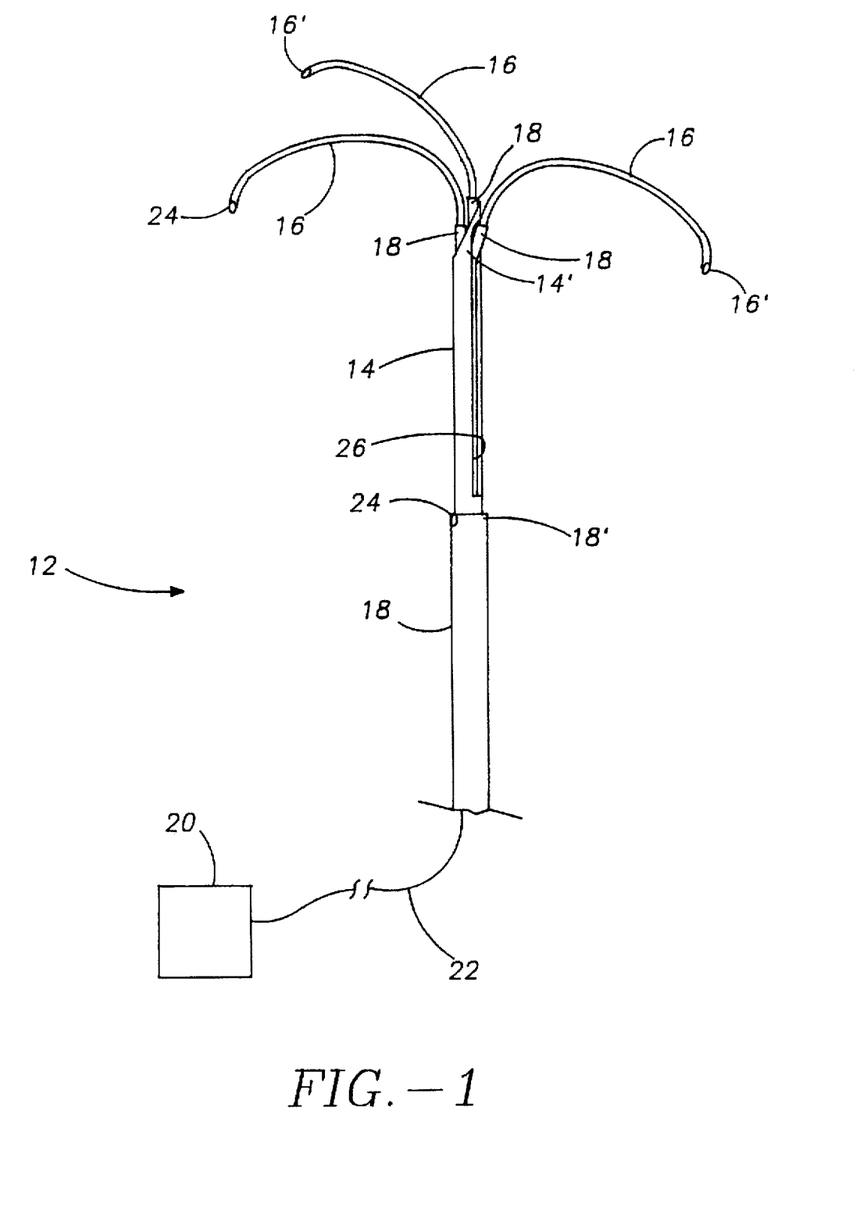
FIG. 1 is a perspective view of the multiple antenna ablation apparatus of the present invention illustrating a trocar and three laterally deployed antennas.

As shown in FIG. 1, multiple antenna ablation device 12 includes a trocar 14, and one or more antennas 16, which are typically electrodes. Antennas 16 are initially positioned in a trocar lumen when trocar 14 is advanced through tissue. When trocar 14 reaches a selected tissue ablation site in a selected tissue mass, including but not limited to a solid lesion, antennas 16 are laterally deployed relative to the trocar's longitudinal axis from the trocar lumen into the selected tissue mass. Volumetric ablation proceeds from the interior of the selected tissue mass in a direction towards a periphery of the selected tissue mass.

Each antenna has a distal end 16' which extends in a lateral direction relative to a longitudinal axis of trocar 14. Unless the distal ends 16' have insulation, then their entire length of extension is an electromagnetic energy delivery surface which delivers electromagnetic energy to the selected tissue mass. The length and size of each electromagnetic energy delivery surface can be variable. Lengths of antennas 16 can be adjustable. Trocar 14 can be moved up and down, rotated about its longitudinal axis, and moved back and forth, in order to define, along with sensors, the periphery or boundary of the selected tissue mass, including but not limited to a tumor. This provides a variety of different geometries, not always symmetrical, that can be ablated.

Volumetric ablation is defined as the creation of an ablation with a periphery formed between adjacent distal ends 16'. The volume of non-ablated tissue between adjacent distal ends 16' is minimized. A variety of different geometric ablations are achieved including but not limited to spherical, semi-spherical, spheroid, triangular, semi-triangular, square, semi-square, rectangular, semi-rectangular, conical, semi-conical, quadrilateral, semi-quadrilateral, semi-quadrilateral, rhomboidal, semi-rhomboidal, trapezoidal, semi-trapezoidal, combinations of the preceding, geometries with non-planar sections or sides, free-form and the like.

In one embodiment, trocar 14 can have a sharpened distal end 14' to assist introduction through tissue. Each antenna 16 has a distal end 16' that can be constructed to be less structurally rigid than trocar 14. Distal end 16' is the section of antenna 16 that is advanced from the lumen antenna 14 and into the selected tissue mass. Distal end is typically less structurally rigid that trocar 14.

Structural rigidity is determined by, (i) choosing different materials for trocar 14 and distal end 16' or some greater length of antenna 16, (ii) using the same material but having less of it for antenna 16 or distal end 16', e.g., antenna 16 or distal end 16' is not as thick as trocar 14, or (iii) including another material in trocar 14 or an antenna 16 to vary their structural rigidity. For purposes of this disclosure, structural rigidity is defined as the amount of deflection that an antenna has relative to its longitudinal axis. It will be appreciated that a given antenna will have different levels of rigidity depending on its length.

Antennas 16 can be made of a variety of conductive materials, both metallic and non-metallic. One suitable material is type 304 stainless steel of hypodermic quality. In some applications, all or a portion of secondary electrode 16 can be made of a shaped memory metal, such as NiTi, commercially available from Raychem Corporation, Menlo Park, Calif.

Each of the antennas 16 can have different lengths. The lengths can be determined by the actual physical length of an antenna 16, the length of an antenna electromagnetic energy delivery surface, and the length of an antenna 16 that is not covered by an insulator. Suitable lengths include but are not limited to 17.5 cm, 25.0 cm, and 30.0 cm. The actual length of an antenna 16 depends on the location of the selected tissue mass to be ablated, its distance from the skin, its accessibility as well as whether or not the physician chooses a laparoscopic, percutaneous or other procedure.

An insulation sleeve 18 may be positioned around an exterior of trocar 14 and/or antennas 16. All or some of insulation sleeves 18 may be adjustably positioned so that the length of an antenna electromagnetic energy delivery surface can be varied. Each insulation sleeve 18 surrounding a trocar 14 can include one or more apertures. This permits the introduction of a antenna 16 through trocar 14 and insulation sleeve 18.

In one embodiment, insulation sleeve 18 comprises a polyamide material. A sensor 24 may be positioned on top of polyimide insulation sleeve 18. The polyamide insulation sleeve 18 is semi-rigid. Sensor 24 can lay down substantially along the entire length of polyamide insulation sleeve 18. Trocar 14 is made of a stainless-steel hypodermic tubing. Antennas 16 have distal ends 16' that are made of NiTi hypodermic tubing. A handle is included with markings to show the length of lateral deployment of antennas 16 from trocar 14. Fluid infusion is delivered through a Luer port at a side of the handle. Type-T thermocouples are positioned at distal ends 16'.

An electromagnetic energy source 20 is connected to multiple antenna device 12 with one or more cables 22. Electromagnetic energy source 20 can be an RF source, microwave source, short wave source, laser source and the like. Multiple antenna device 12 can be comprised of antennas 16 that are RF electrodes, microwave antennas, as well as combinations thereof. Electromagnetic energy source 20 may be a combination RF/microwave box. Further a laser optical fiber, coupled to a laser source 20 can be introduced through one or both of trocar 14 or a antenna 16. Trocar 14 and/or a secondary electrode 16 can be an arm for the purposes of introducing the optical fiber.

Antennas 16 are electromagnetically coupled to electromagnetic energy source 20. The coupling can be direct from electromagnetic energy source 20 to each antenna 16, or indirect by using a collet, sleeve and the like which couples one or more antennas 16 to electromagnetic energy source 20. Electromagnetic energy can be delivered from one antenna 16 to another.

One or more sensors 24 may be positioned on at least a portion of interior or exterior surfaces of trocar 14, antenna 16 or insulation sleeve 18. Preferably sensors 24 are positioned at trocar distal end 14', antenna distal end 16' and insulation sleeve distal end 18'. Sensors 24 permit accurate measurement of temperature at a tissue site in order to determine, (i) the extent of ablation, (ii) the amount of ablation, (iii) whether or not further ablation is needed and (iv) the boundary or periphery of the ablated mass. Further, sensors 24 prevent non-targeted tissue from being destroyed or ablated.

Sensors 24 are of conventional design, including but not limited to thermistors, thermocouples, resistive wires, and the like. Suitable thermal sensors 24 include a T type thermocouple with copper constantene, J type, E type, K type, fiber optics, resistive wires, thermocouple IR detectors, and the like. It will be appreciated that sensors 24 need not be thermal sensors.

Sensors 24 measure temperature and/or impedance to permit monitoring and a desired level of ablation to be achieved without destroying too much tissue. This reduces damage to tissue surrounding the targeted mass to be ablated. By monitoring the temperature at various points within the interior of the selected tissue mass, a determination of the selected tissue mass periphery can be made, as well as a determination of when ablation is complete. If at any time sensor 24 determines that a desired ablation temperature is exceeded, then an appropriate feedback signal is received at electromagnetic energy source 20 which then regulates the amount of electromagnetic energy delivered to antennas 16.

Thus the geometry of the ablated mass is selectable and controllable. Any number of different ablation geometries can be achieved. Creation of different ablation geometries is dependent on the length of electromagnetic energy ablation delivery surfaces, the number of antennas, the size of the electromagnetic delivery surfaces, the amount of power delivered to the antennas, and the duration of time for power delivery to the antennas.

Antenna distal ends 16' can be laterally deployed relative to a longitudinal axis of trocar 14 out of an aperture 26 formed in trocar 14. Aperture 26 is at distal end 14' or formed in a side of an exterior of antenna 14.

In one embodiment, a method for creating a volumetric ablation in a selected tissue mass provides multiple antenna ablation apparatus 12 including trocar 14 with a trocar lumen, a plurality of antennas 16 deployable from the lumen, and an electromagnetic energy source 20 coupled to the plurality of antennas. Trocar 14 is inserted into the selected tissue mass with the plurality of antennas positioned in the trocar 14 lumen. The plurality of antennas 16 are advanced from the trocar lumen in a lateral direction relative to a longitudinal axis of trocar 14 into the selected tissue mass. 10 to 50 watts, preferably 10 to 30, and still more preferably 15 to 20 watts of electromagnetic energy is delivered from electromagnetic energy source 20 to the plurality of antennas 16 without impeding out an antenna of the plurality of antennas. The volumetric ablation is created between the plurality of antennas 16.

There is wide variation in the amount of deflection of antenna 16. For example, antenna 16 can be deflected a few degrees from the longitudinal axis of trocar 14, or antennas 16 can be deflected in any number of geometric configurations, including but not limited to a "J" hook. Further, antennas 16 are capable of being introduced from trocar 14 a few millimeters from trocar 14, or a much larger distance.

Figure 2:
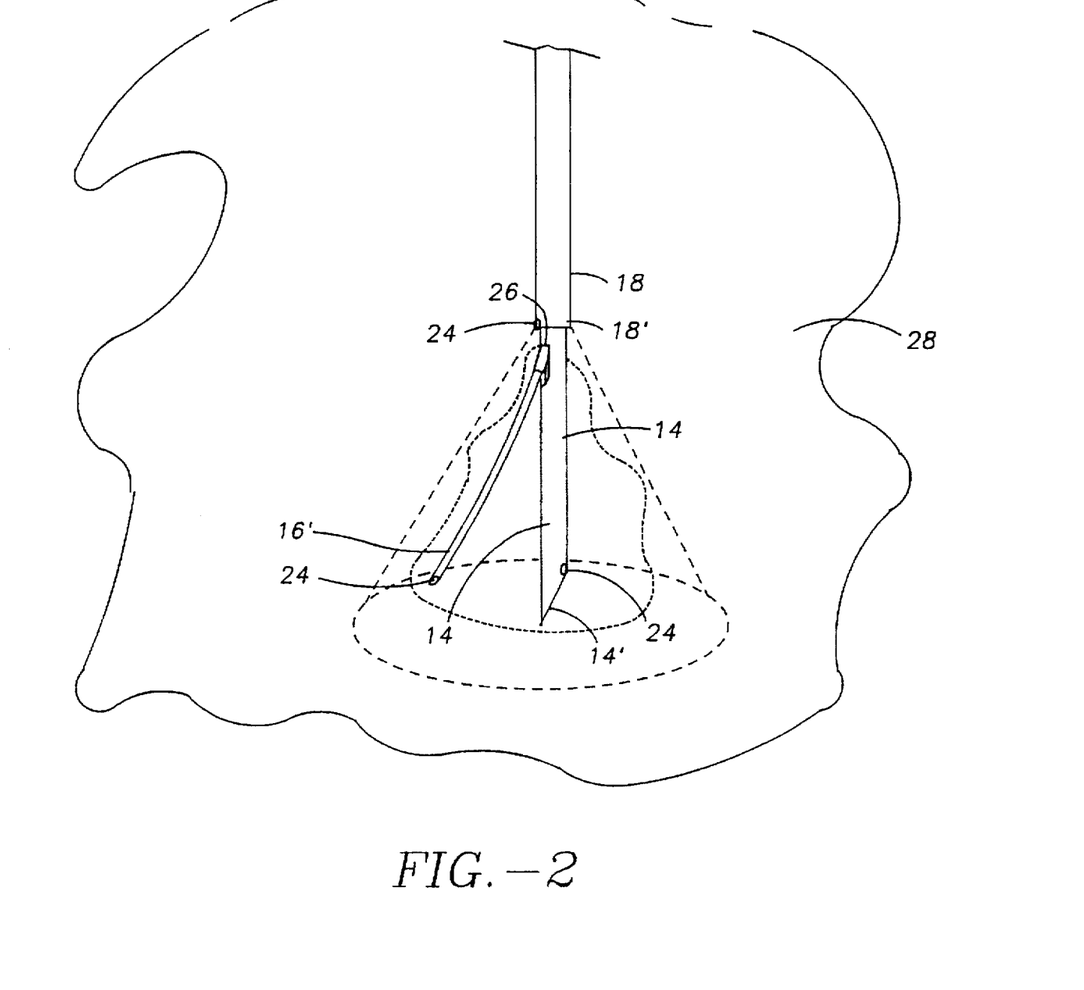
FIG. 2 is a perspective view of a conic geometric ablation achieved with the apparatus of FIG. 1.

As illustrated in FIG. 2, trocar 14 is introduced into a selected tissue mass 28. Three or more antennas 16 are positioned within a trocar lumen as trocar 14 is introduced into and through the selected tissue mass. In various embodiments, 3, 4, 5, or 6 antennas 16 are introduced laterally through trocar 14. Subsequently, antenna distal end 16' is advanced out of aperture 26 into selected tissue mass 28. Insulation sleeves 18 are adjusted for antennas 16. RF, microwave, short wave and the like energy is delivery to antenna 16 in a monopolar mode (RF), or alternatively, multiple antenna device 12 can be operated in a bipolar mode (RF). Multiple antenna device 12 can be switched between monopolar and bipolar operation and may have multiplexing capability between different antennas 16. Antenna distal ends 16' is retracted back into trocar 14, and trocar is then rotated. Antenna distal end 16' is then introduced into selected tissue mass 28. Antennas 16 may be introduced a short distance into selected tissue mass 28 to ablate a small area, e.g., 3 cm or less. It can then be advanced further into any number of times to create more ablation zones. Again, antenna distal end 16' is retracted back into trocar 14, and trocar 14 can be, (i) rotated again, (ii) moved along a longitudinal axis of selected tissue mass 28 to begin another series of ablations with antenna distal ends 16' being introduced and retracted in and out of trocar 14, or (iii) removed from selected tissue mass 28. A number of parameters permit ablation of selected tissue masses 28 of different sign and shapes including a series of ablations having antennas 16 with variable length electromagnetic energy delivery surfaces and the use of one or more sensors 24.

Figure 3:
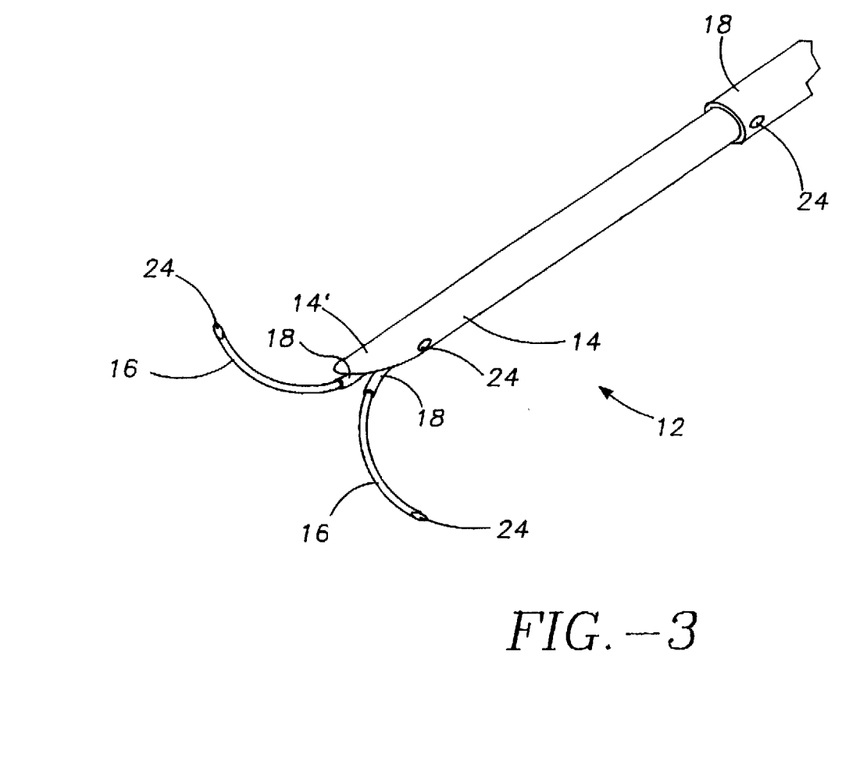
FIG. 3 is a perspective view of the multiple antenna ablation apparatus of the present invention with two antennas.

In FIG. 3, two antennas 16 are each deployed out of distal end 14' and introduced into selected tissue mass 28. Antennas 16 form a plane and the area of ablation extends between the electromagnetic energy delivery surfaces of antennas 16. Trocar 14 can be introduced in an adjacent relationship to selected tissue mass 28. This particular deployment is useful for small selected tissue masses 28, or where piercing selected tissue mass 28 is not desirable. Trocar 14 can be rotated, with antennas 16 retracted in the lumen of trocar 14, and another ablation volume defined between the antennas 16 is created. Further, trocar 14 can be withdrawn from its initial position adjacent to selected tissue mass 28, repositioned to another position adjacent to selected tissue mass 28, and antennas 16 deployed to begin another ablation cycle. Any variety of different positionings may be utilized to create a desired ablation geometry for selected tissue mass of different geometries and sizes.

Figure 4:
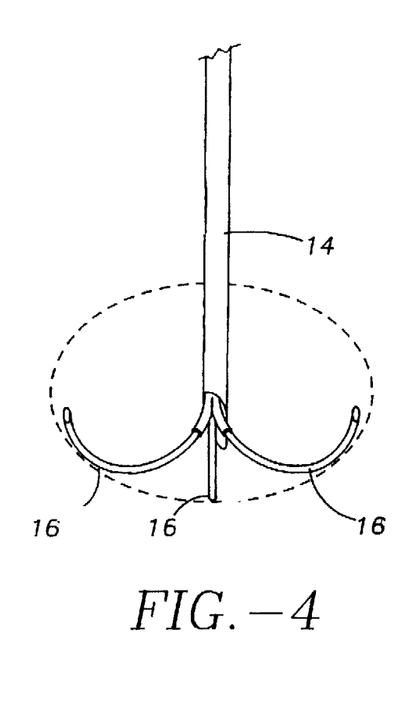
FIG. 4 is a perspective view illustrating three antennas creating a complete ablation volume.

In FIG. 4, three antennas 16 are introduced into selected tissue mass 28. The effect is the creation of a substantially complete ablation volume formed between antennas 16 with a minimal central core that is not ablated.

Figure 5:
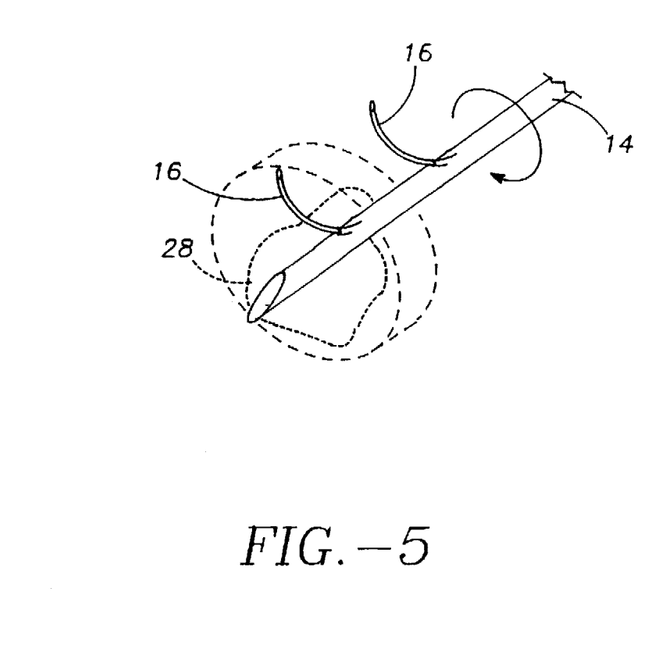
FIG. 5 is a perspective view illustrating the positioning of the multiple antenna ablation apparatus in the center of a selected tissue mass, and the creation of a cylindrical ablation.

Referring now to FIG. 5, a center of selected tissue mass 28 is pierced by trocar 14, antennas 16 are laterally deployed and retracted, trocar 14 is rotated, antennas 16 are deployed and retracted, and so on until a cylindrical ablation volume is achieved. Multiple antenna device 12 can be operated in the bipolar mode between the two antennas 16, or between a antenna 16 and trocar 14. Alternatively, multiple antenna device 12 can be operated in a monopolar mode.

Figure 6A:
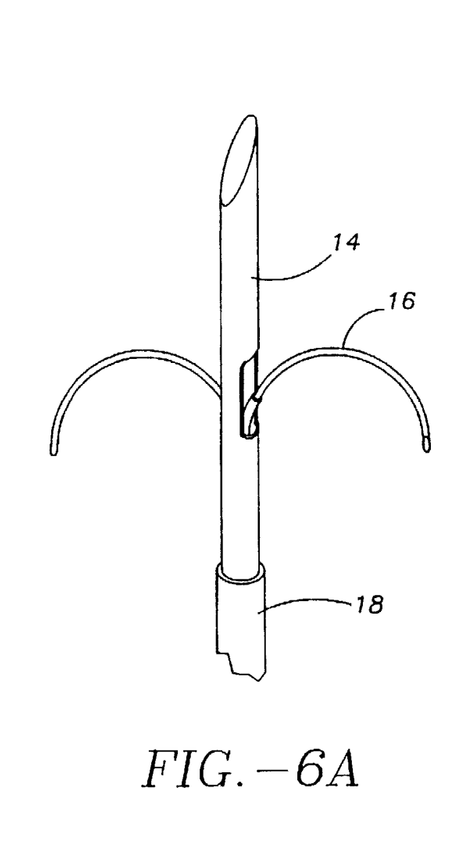
FIG. 6(a) is a perspective view of the multiple antenna ablation of the present invention illustrating two antennas which provide a retaining and gripping function.
Figure 6B:
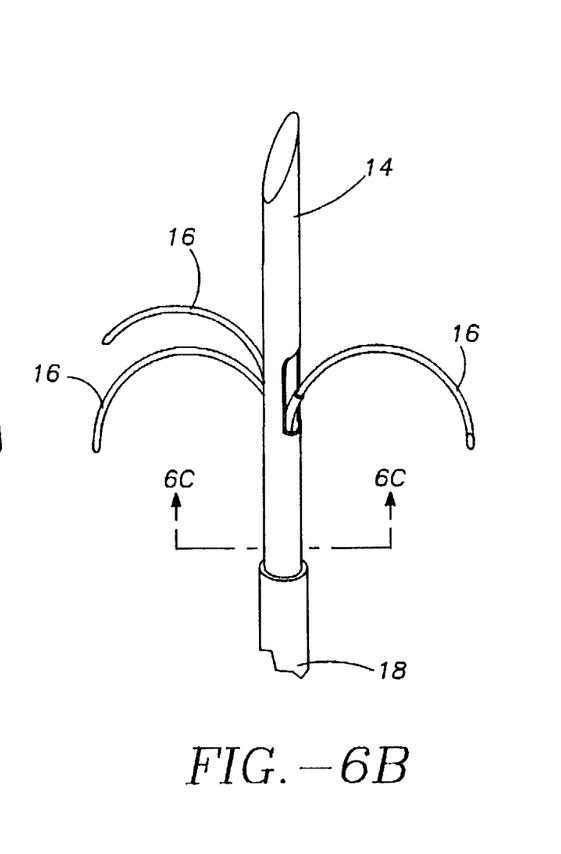
FIG. 6(b) is a perspective view of the multiple antenna ablation of the present invention illustrating three secondary antennas which provide a retaining and gripping function.

Antennas 16 can serve the additional function of anchoring multiple antenna device 12 in a selected mass, as illustrated in FIGS. 6(a) and 6(b). In FIG. 6(a) one or both antennas 16 are used to anchor and position trocar 14. Further, one or both antennas 16 are also used to ablate tissue. In FIG. 6(b), three antennas are deployed and anchor trocar 14.

Figure 6C:
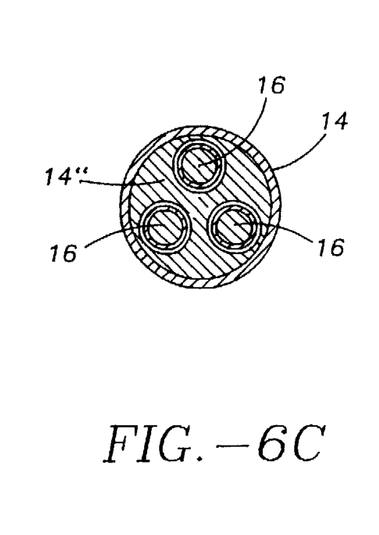
FIG. 6(c) is a cross-sectional view of the apparatus of FIG. 6(b) taken along the lines 6(c)—6(c).

FIG. 6(c) illustrates the infusion capability of multiple antenna device 12. Three antennas 16 are positioned in a central lumen 14" of trocar 14. One or more of the antennas 16 can also include a central lumen coupled to an infusion source. Central lumen 14" is coupled to an infusion source and delivers a variety of infusion mediums to selected places both within and outside of the targeted ablation mass. Suitable infusion mediums include but are not limited to, therapeutic agents, conductivity enhancement mediums, contrast agents or dyes, and the like. An example of a therapeutic agent is a chemotherapeutic agent.

Figure 7:
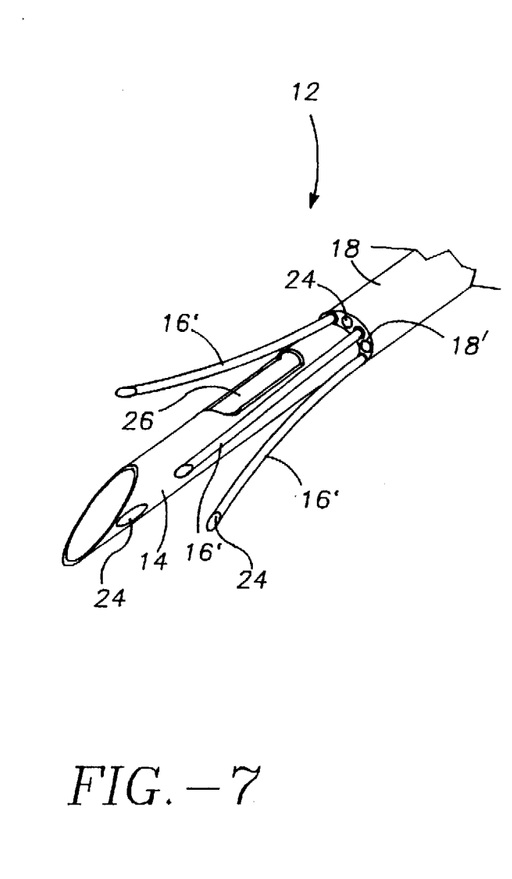
FIG. 7 is a perspective view of the multiple antenna ablation of the present invention illustrating the deployment of three secondary antennas from a distal end of the insulation-sleeve surrounding the primary antenna.
Figure 8:
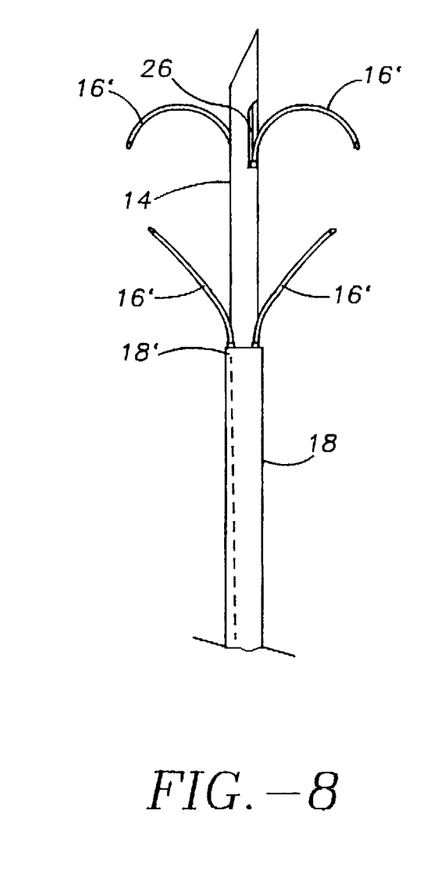
FIG. 8 is a perspective view of the multiple antenna ablation of the present invention illustrating the deployment of two secondary antennas from the primary antenna, and the deployment of three secondary antennas from the distal end of the insulation sleeve surrounding the primary antenna.

As shown in FIG. 7, insulation sleeve 18 can include one or more lumens for receiving antennas 16 which are deployed out of an insulation sleeve distal end 18'. FIG. 8 illustrates two antennas 16 being introduced out of insulation sleeve distal end 18', and two antennas 16 introduced through apertures 26 formed in trocar 14. As illustrated, antennas 16 introduced through apertures 26 provide an anchoring function. FIG. 8 illustrates that antennas 16 can have a variety of different geometric configurations in multiple antenna device 12.

Figure 9:
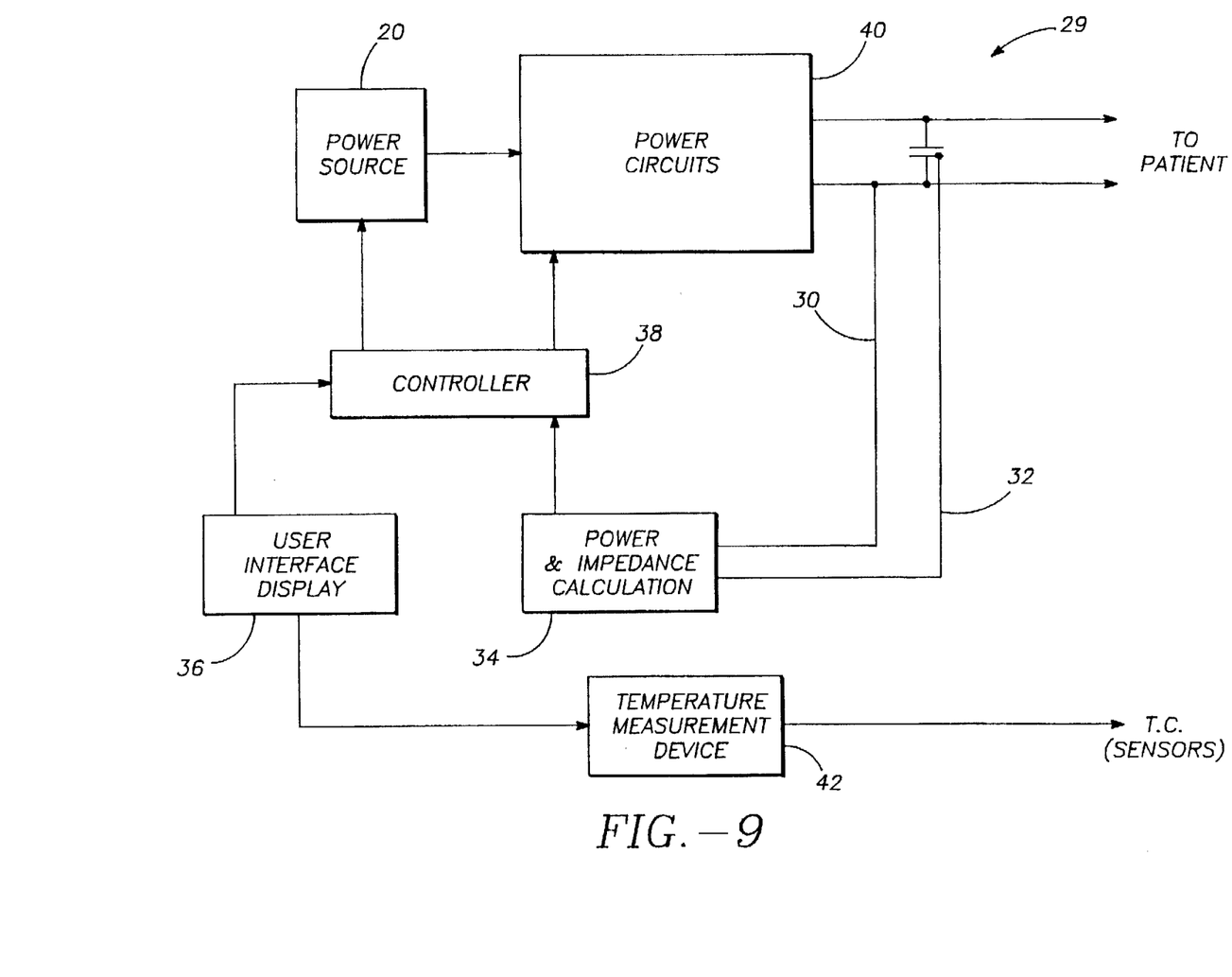
FIG. 9 is a block diagram illustrating the inclusion of a controller, electromagnetic energy source and other electronic components of the present invention.

A feedback control system 29 is connected to electromagnetic energy source 20, sensors 24 and antennas 16. Feedback control system 29 receives temperature or impedance data from sensors 24 and the amount of electromagnetic energy received by antennas 16 is modified from an initial setting of ablation energy output, ablation time, temperature, and current density (the "Four Parameters"). Feedback control system 29 can automatically change any of the Four Parameters. Feedback control system 29 can detect impedance or temperature and change any of the Four Parameters. Feedback control system 29 can include a multiplexer to multiplex different antennas, a temperature detection circuit that provides a control signal representative of temperature or impedance detected at one or more sensors 24. A microprocessor can be connected to the temperature control circuit.

The following discussion pertains particularly to the use of an RF energy source and RF electrodes. It will be appreciated that devices similar to those associated with RF multiple antenna device 12 can be utilized with laser optical fibers, microwave devices and the like.

Referring now to FIG. 9, all or portions of feedback control system 29 are illustrated. Current delivered through antennas 16 is measured by current sensor 30. Voltage is measured by voltage sensor 32. Impedance and power are then calculated at power and impedance calculation device 34. These values can then be displayed at user interface and display 36. Signals representative of power and impedance values are received by controller 38.

A control signal is generated by controller 38 that is proportional to the difference between an actual measured value, and a desired value. The control signal is used by power circuits 40 to adjust the power output in an appropriate amount in order to maintain the desired power delivered at antennas 16.

In a similar manner, temperatures detected at sensors 24 provide feedback for determining the extent of ablation, and when a completed ablation has reached the physical location of sensors 24. The actual temperatures are measured at temperature measurement device 42 and the temperatures are displayed at user interface and display 36. A control signal is generated by controller 38 that is proportional to the difference between an actual measured temperature, and a desired temperature. The control signal is used by power circuits 40 to adjust the power output in an appropriate amount in order to maintain the desired temperature delivered at the respective sensor 24. A multiplexer can be included to measure current, voltage and temperature, at the numerous sensors 24, and energy is delivered to antennas 16.

Controller 38 can be a digital or analog controller, or a computer with software. When controller 38 is a computer it can include a CPU coupled through a system bus. On this system can be a keyboard, a disk drive, or other non-volatile memory systems, a display, and other peripherals, as are known in the art. Also coupled to the bus are a program memory and a data memory.

User interface and display 36 includes operator controls and a display. Controller 38 can be coupled to imaging systems, including but not limited to ultrasound, CT scanners, X-ray, MRI, mammographic X-ray and the like. Further, direct visualization and tactile imaging can be utilized.

The output of current sensor 30 and voltage sensor 32 is used by controller 38 to maintain a selected power level at antennas 16. The amount of RF energy delivered controls the amount of power. A profile of power delivered can be incorporated in controller 38, and a preset amount of energy to be delivered can also be profiled.

Circuitry, software and feedback to controller 38 result in process control, and the maintenance of the selected power, and are used to change, (i) the selected power, including RF, microwave, laser and the like, (ii) the duty cycle (on-off and wattage), (iii) bipolar or monopolar energy delivery and (iv) infusion medium delivery, including flow rate and pressure. These process variables are controlled and varied, while maintaining the desired delivery of power independent of changes in voltage or current, based on temperatures monitored at sensors 24.

Figure 10:
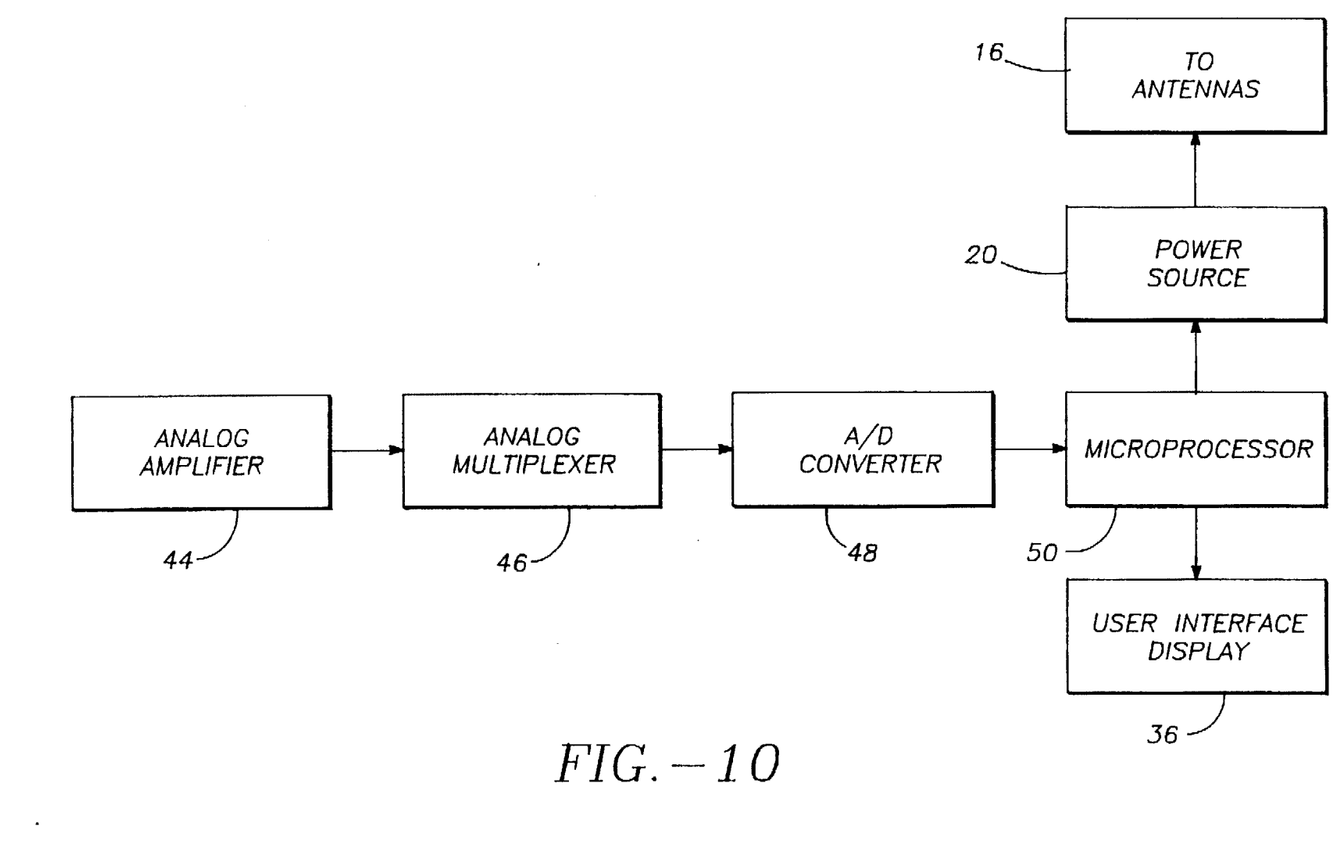
FIG. 10 is a block diagram illustrating an analog amplifier, analog multiplexer and microprocessor used with the present invention.

Referring now to FIG. 10, current sensor 30 and voltage sensor 32 are connected to the input of an analog amplifier 44. Analog amplifier 44 can be a conventional differential amplifier circuit for use with sensors 24. The output of analog amplifier 44 is sequentially connected by an analog multiplexer 46 to the input of A/D converter 48. The output of analog amplifier 44 is a voltage which represents the respective sensed temperatures. Digitized amplifier output voltages are supplied by A/D converter 48 to a microprocessor 50. Microprocessor 50 may be Model No. 68HCII available from Motorola. However, it will be appreciated that any suitable microprocessor or general purpose digital or analog computer can be used to calculate impedance or temperature.

Microprocessor 50 sequentially receives and stores digital representations of impedance and temperature. Each digital value received by microprocessor 50 corresponds to different temperatures and impedances.

Calculated power and impedance values can be indicated on user interface and display 36. Alternatively, or in addition to the numerical indication of power or impedance, calculated impedance and power values can be compared by microprocessor 50 with power and impedance limits. When the values exceed predetermined power or impedance values, a warning can be given on user interface and display 36, and additionally, the delivery of RF energy can be reduced, modified or interrupted. A control signal from microprocessor 50 can modify the power level supplied by electromagnetic energy source 20.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An ablation treatment apparatus, comprising:

a trocar including a distal end sharp enough to pierce tissue, and a hollow lumen extending along a longitudinal axis of the trocar;

a multiple antenna ablation device including three or more antennas, each antenna including a distal portion and each antenna being at least partially positioned in the trocar lumen as the trocar is introduced through tissue, at least a part of each distal portion of a deployed antenna being configured to be deployable from the trocar lumen at a selected tissue site with at least one radius of curvature and having a deployed antenna electromagnetic energy delivery surface, wherein a collective size of the deployed antennas' electromagnetic energy delivery surfaces is sufficient to create a volumetric ablation between the deployed antennas without impeding out a deployed antenna when 10 to 50 watts of electromagnetic energy is delivered from an electromagnetic energy source to the multiple antenna ablation device; and at least one cable coupling the multiple antenna ablation device to the electromagnetic energy source.

2. The apparatus of claim 1, wherein the collective size of the deployed antennas' electromagnetic energy delivery surfaces is sufficient to create a volumetric ablation between the deployed antennas without impeding out a deployed antenna when 10 to 30 watts of electromagnetic energy is delivered from the electromagnetic energy source to the multiple antenna ablation device.

3. The apparatus of claim 1, wherein the collective size of the deployed antennas' electromagnetic energy delivery surfaces is sufficient to create a volumetric ablation between the deployed antennas without impeding out a deployed antenna when 15 to 20 watts of electromagnetic energy is delivered from the electromagnetic energy source to the multiple antenna ablation device.

4. The apparatus of claim 1, wherein each of the antennas is coupled to the electromagnetic energy source.

5. The apparatus of claim 1, wherein the trocar has an outer diameter no greater than 13 gauge.

6. The apparatus of claim 1, wherein the trocar has an outer diameter no greater than 14 gauge.

7. The apparatus of claim 1, wherein the trocar has an outer diameter no greater than 15 gauge.

8. The apparatus of claim 1, wherein four deployed antennas are deployed from the trocar at the selected tissue mass.

9. The apparatus of claim 8, wherein at least one deployed antenna is deployed into the selected tissue mass from the trocar distal end and at least one deployed antenna is deployed into the selected tissue mass from a side port.

10. The apparatus of claim 1, wherein five deployed antennas are deployed from the trocar at the selected tissue mass.

11. The apparatus of claim 1, wherein six deployed antennas are deployed from the trocar at the selected tissue mass.

12. The apparatus of claim 1, wherein at least two of the deployed antennas are deployed out of the trocar distal end.

13. The apparatus of claim 1, wherein the trocar includes one or more side ports formed in a body of the trocar.

14. The apparatus of claim 1, wherein the antennas are RF electrodes and the electromagnetic energy source is an RF energy source.

15. The apparatus of claim 1, wherein the multiple antenna ablation device operates in a monopolar mode.

16. The apparatus of claim 1, wherein the multiple antenna ablation device operates in a bipolar mode.

17. The apparatus of claim 1, wherein the apparatus is switchable between bipolar and monopolar operation.

18. The apparatus of claim 1 wherein at least a part of a distal portion of each deployed antenna is constructed to be structurally less rigid than the trocar.

19. The apparatus of claim 1, further comprising:
a sensor at least partially positioned on an exterior surface of a deployed antenna.

20. The apparatus of claim 1, further comprising:
an insulation layer positioned in a surrounding relationship around at least a portion of an exterior of the trocar.

21. The apparatus of claim 20, wherein a distal end of the insulation layer is removed from the distal end of the trocar and create an electromagnetic energy delivery surface at the distal end of the trocar.

22. The apparatus of claim 1, wherein the trocar lumen is coupled to an infusion medium source to receive an infusion medium.

23. The apparatus of claim 1, further comprising:
a cooling element coupled to at least a portion of the trocar.

24. The apparatus of claim 23, wherein the cooling element comprises:
a structure at least partially positioned in the trocar including at least one channel configured to receive a cooling medium.

25. The apparatus of claim 24, wherein the cooling medium is recirculated through the channel.

26. An ablation treatment apparatus, comprising:
a trocar including a distal end sharp enough to pierce tissue, and a hollow lumen extending along a longitudinal axis of the trocar;

a multiple antenna ablation device including a plurality of antennas, each antenna including a distal portion and each antenna being at least partially positioned in the trocar lumen as the trocar is introduced through tissue, at least a part of each distal portion of a deployed antenna being configured to be deployable from the trocar lumen at a selected tissue site with at least one radius of curvature, wherein the plurality of antennas includes a sufficient number of antennas to create an ablation volume between the antennas in the selected tissue site without impeding out the plurality of antennas when 10 to 50 watts of electromagnetic energy is delivered from the electromagnetic energy source to the plurality of antennas; and at least one cable coupling the multiple antenna ablation device to the electromagnetic energy source.

27. The apparatus of claim 26, wherein the trocar has an outer diameter no greater than 15 gauge.

28. The apparatus of claim 26, wherein the multiple antenna ablation device is an RF device.

29. The apparatus of claim 28, wherein the multiple antenna ablation device operates in a monopolar mode.

30. The apparatus of claim 28, wherein the multiple antenna ablation device operates in a bipolar mode.

31. The apparatus of claim 28, wherein the multiple antenna ablation device is switchable between bipolar and monopolar operation.

32. A method for creating a volumetric ablation in a selected tissue mass, comprising:
providing a multiple antenna ablation apparatus including a trocar with a trocar lumen, a plurality of antennas deployable from the lumen, and an electromagnetic energy source coupled to the plurality of antennas;

inserting the trocar into the selected tissue mass with the plurality of antennas positioned in the trocar lumen;

advancing the plurality of antennas from the trocar lumen in a lateral direction relative to a longitudinal axis of the trocar into the selected tissue mass;

delivering 10 to 50 watts of electromagnetic energy from the electromagnetic energy source to the plurality of antennas without impeding out an antenna of the plurality of antennas; and creating the volumetric ablation in the selected tissue mass.

33. The method of claim 32, wherein the ablation volume is a spheroid geometry.

34. The method of claim 32, wherein the ablation volume is a spherical geometry.

35. The method of claim 32, wherein the ablation volume is a partial spherical geometry.

36. The method of claim 32, wherein the ablation volume is formed continuously between adjacently deployed antennas of the plurality.

37. The method of claim 32, wherein the trocar has an outer diameter no greater than 15 gauge.

38. The method of claim 32, wherein each antenna of the plurality has an electromagnetic energy delivery surface size sufficient to receive 10 to 50 watts of electromagnetic energy from the electromagnetic energy source.

* * * * *